US010696734B2

(12) United States Patent
Sand et al.

(10) Patent No.: US 10,696,734 B2
(45) Date of Patent: *Jun. 30, 2020

(54) SECRETORY IGA COMPOSITIONS, METHODS OF MAKING AND METHODS OF USE THEREOF

(71) Applicant: Wisconsin Alumni Research Foundation, Madison, WI (US)

(72) Inventors: Jordan Marshall Sand, Madison, WI (US); Mark Eric Cook, Madison, WI (US)

(73) Assignee: WISCONSIN ALUMNI RESEARCG FOUNDATION, Madison, WI (US)

(*) Notice: Subject to any disclaimer, the term of this patent is extended or adjusted under 35 U.S.C. 154(b) by 208 days.

This patent is subject to a terminal disclaimer.

(21) Appl. No.: 15/249,811

(22) Filed: Aug. 29, 2016

(65) Prior Publication Data

US 2016/0362477 A1  Dec. 15, 2016

Related U.S. Application Data

(62) Division of application No. 13/734,426, filed on Jan. 4, 2013, now Pat. No. 9,458,230.

(51) Int. Cl.

| C07K 16/00 | (2006.01) |
|---|---|
| C07K 16/18 | (2006.01) |
| C07K 1/30 | (2006.01) |
| A23K 20/147 | (2016.01) |
| A23K 50/20 | (2016.01) |
| A23K 50/10 | (2016.01) |
| A23K 50/75 | (2016.01) |
| A23K 50/30 | (2016.01) |
| A23K 50/40 | (2016.01) |
| A23K 50/80 | (2016.01) |
| A23L 33/17 | (2016.01) |
| A61K 39/00 | (2006.01) |

(52) U.S. Cl.
CPC ............ *C07K 16/00* (2013.01); *A23K 20/147* (2016.05); *A23K 50/10* (2016.05); *A23K 50/20* (2016.05); *A23K 50/30* (2016.05); *A23K 50/40* (2016.05); *A23K 50/75* (2016.05); *A23K 50/80* (2016.05); *A23L 33/17* (2016.08); *C07K 1/30* (2013.01); *C07K 16/18* (2013.01); *A23V 2002/00* (2013.01); *A61K 2039/505* (2013.01); *C07K 2317/10* (2013.01); *C07K 2317/20* (2013.01)

(58) Field of Classification Search
None
See application file for complete search history.

(56) References Cited

U.S. PATENT DOCUMENTS

| 3,658,551 A | 4/1972 | Bundus et al. |
|---|---|---|
| 5,258,177 A | 11/1993 | Uemura et al. |
| 5,607,840 A | 3/1997 | Van Gorp et al. |
| 6,300,104 B1* | 10/2001 | Morrison ......... A61K 39/39591 424/133.1 |
| 8,313,730 B2 | 11/2012 | Simon et al. |
| 9,468,674 B2* | 10/2016 | Cook .................. A61K 39/395 |
| 2001/0049119 A1 | 12/2001 | Lee et al. |
| 2008/0145371 A1 | 6/2008 | Simon |
| 2008/0145420 A1 | 6/2008 | Simon |
| 2010/0303830 A1* | 12/2010 | Bruessow .......... C07K 16/1214 424/164.1 |
| 2011/0256269 A1* | 10/2011 | Medo ...................... A23C 3/02 426/72 |
| 2011/0305753 A1 | 12/2011 | Simon |
| 2012/0014963 A1 | 1/2012 | Benyacoub et al. |
| 2012/0045517 A1* | 2/2012 | Simon ................. C07K 16/065 424/499 |
| 2012/0141458 A1* | 6/2012 | Starzl .................... C07K 16/10 424/130.1 |
| 2014/0193395 A1 | 7/2014 | Sand et al. |
| 2016/0318994 A1 | 11/2016 | Cook et al. |

FOREIGN PATENT DOCUMENTS

| CN | 101044900 A | 10/2007 |
|---|---|---|
| CN | 101045750 A | 10/2007 |
| CN | 102076360 A | 5/2011 |
| CN | 102124027 A | 7/2011 |
| EP | 0479597 A2 | 4/1992 |
| EP | 2138186 A1 | 12/2009 |
| JP | 58187145 | 1/1983 |
| JP | 2009210554 A | 9/2009 |
| RU | 2005109538 A | 11/2006 |
| WO | 2002063948 A2 | 8/2002 |

(Continued)

OTHER PUBLICATIONS

Maoke Liu, "Establishment and application of direct ELISA for detection of pig SIgA" 42(2), pp. 154-159, 2012 (Year: 2012).*
Willian Doe "The intestinal immune system" Gut, 1989, 30, pp. 1679-1685 (Year: 1989).*
Czank et al. "Retention of the immunological proteins of pasteurized human milk in relation to pasteurizer design and practice" 65(4) 2009, pp. 374-379 (Year: 2009).*
Corthesy, Blaise; "Multi-faceted Functions of Secretory IgA at Mucosal Surfaces"; Frontiers in Immunology; vol. 4, Article 185, 11 pages; (2013).
Berneman, et al.; "The Specificity Patterns of Human Immunoglobulin G Antibodies in Serum Differ from Those in Autologous Secretions"; Infection and Immunity; pp. 4163-4168; (1998).
Definition of Feed efficiency, found in "Introduction to Animal Science"; Third Edition; W. Stephen Damron, Ed.; Pearson, Prentice Hall; p. 785; 2006.

(Continued)

Primary Examiner — Daniel E Kolker
Assistant Examiner — James L Rogers
(74) Attorney, Agent, or Firm — Cantor Colburn LLP

(57) ABSTRACT

Described herein is secretory IgA isolated from the intestinal luminal fluid and intestinal mucosal of animals such as pigs and cows. Also included are methods of isolating secretory IgA. The secretory IgA is useful in food compositions such as animal and human food compositions as well as pharmaceutical compositions to increase growth rate, improve feed efficiency, reduce gastrointestinal inflammation, reduce a risk of gastrointestinal infection in the animal, or a combination thereof.

9 Claims, No Drawings

(56) References Cited

FOREIGN PATENT DOCUMENTS

| WO | 2004000035 A1 | 12/2003 |
|---|---|---|
| WO | 2009156301 A1 | 12/2009 |
| WO | 2012080306 A1 | 6/2012 |
| WO | 2013087911 A1 | 6/2013 |
| WO | 2013132052 A1 | 9/2013 |
| WO | 20140107269 A1 | 7/2014 |

OTHER PUBLICATIONS

Karczewski, Jerry; "Animal-Derived Medicines Play a Critical Role in Human Health Care"; Meat+Poultry; Jan. 2017; pp. 16-22; www.meatpoultry.com; (2017).
Cripps et al.; "The Origin of Immunoglobulin in Intestinal Secretion of Sheep"; Ajebak; 51(4); pp. 711-716; (1974).
Ahmadi et al.; "Benefits of Bovine Colostrum in Nutraceutical Products"; Journal of Agroalimentary Processes and Technologies; 17(1), pp. 42-45, (2011).
Ananthakrishnan et al.; "How does Genotype Influence Disease Phenotype in Inflammatory Bowel Disease?"; Inflamm Bowel Dis; 19(9);pp. 2021-2030; (2013).
Balan et al.; "Orally Administered Ovine Serum Immunoglobulins Influence Growth Performance, Organ Weights, and Gut Morphology in Growing Rats"; Journal of Nutrition; 139(2); pp. 244-249; (2008).
Beetham et al.; "A Comparison of Three Isolation Methods for Obtaining Immunoglobulin a From Turkey Bile"; Avian Diseases; 37(4); pp. 1026-1031; (1993).
Bodammer et al.; "Alteration of DSS-mediated Immune Cell Redistribution in Murine Colitis by Oral Colostral Immunoglobulin"; BMC Immunology, Biomed Central 14(1); p. 10 (2013).
Boullier et al; "Secretor IgA-Mediated Neutralization of Shigella flexneri Prevents Intestinal Tissue Destruction by Down-Regulating Inflammatory Circuits"; Journal of Immunology; 183(9); pp. 5879-5885; (2009).
Bourne et al.; "Intestinal Immunoglobulins in the Pig"; Biochim. Biophys. Acta; 229; pp. 18-25; (1971).
Cerutti et al.; "Regulation of Mucosal IgA Responses: Lessons from Primary Immunodeficiencies"; Ann. N.Y. Acad. Sci.; 1238; pp. 132-144; (2011).
Ferm-O-Tide XP, Products Information Sheet by Midwest AG Enterprises; http://midwestagenterprises.com/ferm-o-tideXP.tml; printed Jan. 22, 2013; 1 page.
Hofmann, Michael; High Quality Supplementary Feed Line with Colostrum: LR Brings Professional on the Animal Market (With Picture); na Presseportal; pp. 1-3; (2011); http://www.presseportal.de/pm/76151/2034045; google translation.
International Search Report and Written Opinion; International Application No. PCT/US2013/073807; International Filing Date Dec. 9, 2013; dated Apr. 10, 2014; 23 pages.
Kanamaru, et al.; "Some Properties of Secretory IgA Purified from Bovine Colostrum"; Agric. Biol. Chem.; 46(8); pp. 2009-2014; (1982).
Kim et al.; "Optimal Dietary Ratio of Spray Dried Plasma Protein (DSPP) and Dried Porcine Solubles (DPS) in Improving Growth Performance and Immune Status in Pigs Weaned at 21 Days of Age"; Asian-Aust. Journal of Animal Sciences; 14(3); pp. 338-345; (2001).
Kuitunen et al.; "High Intestinal IgA Associates with Reduced Risk of IgE-Associated Allergic Diseases"; Pediatr Allergy Immunol; 21; pp. 67-73; (2010).
Kull et al.; "Breast-feeding Reduces the Risk for Childhood Eczema"; Journal of Allergy and Clinical Immunology; 116(3); pp. 657-661; (2005).
Linhardt et al.; "Production and Chemical Processing of Low Molecular Weight Heparins"; Seminars in Thrombosis and Hemostasis; 25(3); pp. 5-16; (1999).
Lundell et al.; "High Circulating Immunoglobulin a Levels in Infants Are Associated With Intestinal Toxigenic Aureus and a Lower Frequency of Eczema"; Clinical & Experimental Allergy; 39; pp. 662-670; (2009) Staphylococcus.
Luoviksson et al.; "Allergic Diseases and Asthma in Relation to Serum Immunoglobulins and Salivary Immunoglobulin A in Pre-School Children: a Follow-Up Community-Based Study"; Clin Exp Allergy; 35; pp. 64-69; (2005).
Mantis et al.; "Secretory IgA's Complex Roles in Immunity and Mucosal Homoeostasis in the Gut"; Mucosal Immunol.; 4(6); 603-611; (2011).
Marschan et al.; "Probiotics in Infancy Induce Protective Immune Profiles That Are Characteristic for Chronic Low-Grade Inflammation"; Clinical and Experimental Allergy; 38; pp. 611-618; (2008).
Marsella et al.; "Investigation of the Effect of Probiotic Exposure on Filaggrin Expression in an Experimental Model of Canine Atopic Dermatitis"; Vet Dermatol; 24; pp. 260-e57; (2013).
Mestecky et al.; "Intestinal IgA: Novel Views on Its Function in the Defence of The Largest Mucosal Surface"; Gut; 44; pp. 2-5; (1999).
Pierce et al.; "Effects of Spray-Dried Animal Plasma and Immunoglobulins on Performance of Early Weaned Pigs"; Journal of Animal Science; 83; pp. 2876-2885; (2005).
Porter et al.; "Intestinal Secretion of Immunoglobulins and Antibodies to *Escherichia coli* in the Pig"; Immunology; 18; pp. 909-920; (1970).
RU2005109538 (A); published Sep. 10, 2006; English Abstract only; 3 pages.
Sulabo et al.; "Nutritional Value of Dried Fermentation Biomass, Hydrolyzed Porcine Intestinal Musoca Products, and Fish Meal Fed to Weanling Pigs"; J ANIM SCI Published online Sep. 5, 2012; 29 pages.
Wold et al.; "Breast Feeding and the Intestinal Microflora of the Infant—Implications for Protection Against Infectious Diseases"; Adv Exp Med Biol; 478; pp. 77-93; (2000).
Yano et al.; "Population Sizes and Growth Pressure Responses of Intestinal Microfloras of Deep-Sea Fish Retrieved from the Abyssal Zone"; Applied and Environmental Microbiology; pp. 4480-4483; (1995).
Yao et al.; "Isolation and Purification of Bovine Colostrum sIgA and IgG"; Journal of Northeast Agricultural University; 15(1); pp. 58-61; (2008).
Yel, Leman; "Selective IgA Deficiency"; J. Clin Immunol; 30; pp. 10-16; (2010).

* cited by examiner

US 10,696,734 B2

SECRETORY IGA COMPOSITIONS, METHODS OF MAKING AND METHODS OF USE THEREOF

CROSS-REFERENCE TO RELATED APPLICATIONS

This application is a divisional of U.S. application Ser. No. 13/734,426 filed on Jan. 4, 2013, which is incorporated herein by reference in its entirety.

FIELD OF THE DISCLOSURE

The present disclosure is related to methods of producing secretory IgA, purified secretory IgA, compositions comprising secretory IgA, and methods of use thereof.

BACKGROUND

Immunoglobulin A is the most abundant of the five classes of immunoglobulin and is primarily found in the mucosa of the gastrointestinal tract and the respiratory tract. There are two types of immunoglobulin A, secretory IgA and serum IgA. Serum IgA is generally a monomer found in the serum of many species, where it functions as a second line of defense which mediates the elimination of pathogens that have breached the mucosal surface. Secretory IgA (SIgA) is dimeric or polymeric and contains a secretory component in addition to IgA. SIgA is a common constituent of breast milk for the young and a secreted protein into the gastrointestinal system during post-weaned development and adulthood. It has been suggested that systemic administration of IgA may be protective against the progression of inflammation that leads to septic shock. Currently there is no method devised to correct a deficiency of SIgA in the gastrointestinal tract of animals and humans and no evidence that said administration can correct these disorders.

SIgA has been shown to bind a wide variety of environmental proteins and polysaccharides (e.g., bacteria, viruses, toxins, food components) preventing their entry into the body and the activation of host inflammatory immune mechanisms. Currently, there is no mechanism known for the production of SIgA with a diverse range of antigen binding activity apart from synthesis in an animal (e.g., SIgA with diverse antigen binding activity cannot be produced using chemistry, recombinant microorganism in fermentation or stem cells). Further, the more diverse the exposure of an animal to environmental insult the greater the repertoire and diversity of SIgA activity. To explore the use of SIgA as a dietary/oral supplement for the treatment of disease, there must be a source of SIgA that can be directly collected from an animal. In addition, it is advantageous that the amount of material collected is cost effective relative to the treatment of the disease malady because many diseases treatable with SIgA are not life threatening enough to warrant costly pharmaceutical therapy.

What is needed is a source of SIgA that can be used as a supplement to treat SIgA related disorders.

BRIEF SUMMARY

In one aspect, a composition comprises pure, optionally pasteurized secretory IgA isolated from intestinal luminal fluid or intestinal mucosa of a pig or a cow.

In another aspect, included herein is secretory IgA isolated from a source that is intestinal mucosa of a pig or a cow, wherein the concentration of secretory IgA in the isolated secretory IgA is at least twice the concentration in the source material, wherein the source material is dried intestinal mucosa, an aqueous preparation of proteins prepared from intestinal mucosa, or a dry preparation of proteins prepared from intestinal mucosa.

In yet another aspect, a food composition comprises a basal food composition, and an amount of secretory IgA effective to increase growth rate, improve feed efficiency, reduce gastrointestinal inflammation, reduce a risk of gastrointestinal infection in the animal, or a combination thereof.

In a still further aspect, a method of increasing growth rate, improving feed efficiency, reducing gastrointestinal inflammation, reducing a risk of gastrointestinal infection, or a combination thereof in a subject, comprises administering to the subject an amount of secretory IgA effective to increase growth rate, improve feed efficiency, reduce gastrointestinal inflammation, reduce a risk of gastrointestinal infection, or a combination thereof in the subject.

In another aspect, a method of increasing growth rate, improving feed efficiency, reducing gastrointestinal inflammation, reducing a risk of gastrointestinal infection, or a combination thereof in an animal, comprises administering to the animal dried intestinal mucosa from a pig or a cow, wherein the dried intestinal mucosa is not hydrolyzed, and wherein the dried intestinal mucosa contains an amount of secretory IgA effective to increase growth rate, improve feed efficiency, reduce gastrointestinal inflammation, reduce a risk of gastrointestinal infection, or a combination thereof in the animal.

In a further aspect, a process for purifying secretory IgA, comprises treating the intestinal luminal fluid of a pig with polyethylene glycol having a molecular weight of 3000 to 30,000 to precipitate the secretory IgA, and isolating the precipitated secretory IgA. In another aspect, a method of preparing an animal food comprises drying unhydrolyzed pig or cow intestinal mucosa, and adding the dried, unhydrolyzed pig or cow intestinal mucosa to a basal animal food composition.

The above-described and other features will be appreciated and understood by those skilled in the art from the following detailed description, drawings, and appended claims.

DETAILED DESCRIPTION

Described herein are compositions comprising SIgA and methods for the purification of SIgA from the intestinal luminal fluid or intestinal mucosa of animals such as pigs and cows. SIgA is an immunoglobulin with diverse antigen binding activity. When SIgA is released from the mucosa to the external environment, it forms immune complexes with pathogens, food antigens and allergens, thereby preventing them from binding to and penetrating the intestinal mucosa. Thus, purified SIgA can be used to supplement SIgA deficiency and to improve weight gain and/or feed efficiency in animals.

Currently, pig and cow intestines are typically used as a source of heparin. Heparin is a highly sulfated glycosaminoglycan, widely used as an anticoagulant. Like SIgA, heparin cannot be produced by modern chemical methods and is isolated from biological sources. Heparin is typically purified from whole pig intestine or the endothelial lining (mucosa) using a procedure that involves elevated temperature, elevated pressure, and/or proteases to separate the heparin from the tissue. Final purification typically involves use of a cation exchange resin. The goal of the present application was to isolate SIgA from the intestinal luminal fluid during the preparation of intestines for heparin extraction as well as from the intestinal mucosa.

As used herein, intestinal luminal fluid is the fluid found within the intestinal lumen of an animal. The lumen is the interior cavity of the intestine where digested food passes through and nutrients are absorbed. The composition of intestinal luminal fluid varies depending on the diet, fed/fasted state and the disease state of the organism. Intestinal luminal fluid contains, for example, lipids; proteins including SIgA; bacteria; ions such as sodium, potassium and calcium; and solid undigested materials.

Also as used herein, intestinal mucosa refers to the inner wall (luminal lining) of the intestine. The intestine includes an outer wall called the serosa, middle muscle layers, and an interior called the mucosa.

In one embodiment, described herein is a composition comprising isolated and/or pure SIgA. Isolated or pure SIgA is isolated or purified from the intestinal luminal fluid or the intestinal mucosa of a pig or a cow.

As used herein, the term "isolated" protein includes protein molecules that are separated from at least a fraction of the other protein or non-protein molecules present in the natural source of the protein. An isolated protein is free of a substantial amount of the cellular material or other contaminating polypeptides from the cell, tissue, or bodily fluid source from which the protein is derived. Isolated SIgA may have a concentration of SIgA twice the concentration in the source material, that is, twice the concentration of SIgA in source intestinal mucosa or luminal fluid. In other embodiments, isolated SIgA, has a concentration three, four, five, ten or more-fold compared to the concentration in the source intestinal mucosa.

In one embodiment, secretory IgA isolated from a source that is intestinal mucosa of a pig or a cow, wherein the concentration of secretory IgA in the isolated secretory IgA is at least twice the concentration in the source material, wherein the source material is dried intestinal mucosa, an aqueous preparation of intestinal mucosa, or a dry preparation of proteins prepared from intestinal mucosa.

In one embodiment, an isolated SIgA preparation is a dry preparation sourced from intestinal mucosa, wherein 5% or more of the proteinaceous material in the isolated SIgA comprises IgA. Without being held to theory, it is believed that there are 5-10 g of SIgA for every 100 g of mucosal protein. In other embodiments, greater than 10, 20, 30, 40, 50, 60, 70, 80, 90 or 95% of the proteinaceous material in the isolated SIgA comprises IgA.

The term pure with reference to SIgA means that SIgA is isolated and that the SIgA components (IgA and secretory components) comprise greater than 75%, specifically greater than 85% and more specifically greater than 95% of the protein in the sample. Pure SIgA can be prepared from intestinal mucosa or intestinal luminal fluid.

In one embodiment, the pure SIgA preparation is pasteurized. Pasteurization is a process of heating a liquid to a specific temperature for a defined length of time and then substantially immediately cooling the liquid. The goal of pasteurization is to reduce the number of viable pathogens in a liquid. Exemplary conditions for pasteurization are 50-100° C. for 5-30 seconds or 120-150° C. for 1-8 seconds, for shelf stable pasteurization. As shown herein, pasteurization of the SIgA isolated from pig intestinal mucosa can be important in the use of the SIgA preparations to increase feed efficiency in chicks.

In one embodiment, the pure SIgA composition has a secretory IgA lipopolysaccharide (LPS) binding activity at least 5 times greater than serum IgA lipopolysaccharide binding activity. An indirect ELISA can demonstrate the LPS binding activity. LPS is coated on a microtiter plate. Either intestinal SIgA or serum IgA is added at various dilutions to the LPS bound on the microtiter plate. After unbound SIgA is removed by washing, the amount of SIgA that bound to the plate bound LPS is detected using an anti-IgA antibody conjugated to an enzyme like horseradish peroxidase plus substrate. Increased binding is when a given amount intestinal SIgA has higher binding capacity relative to the same amount of serum IgA.

In one embodiment, the pure, pasteurized SIgA is in the form of a pharmaceutical composition comprising a pharmaceutically acceptable excipient.

In one embodiment, a process for purifying a SIgA composition comprises treating the intestinal luminal fluid of a pig or cow with polyethylene glycol having a molecular weight of 3000 to 30,000, and isolating the precipitated SIgA. In one embodiment, the SIgA is enriched at least two-fold compared to the concentration of SIgA in the intestinal luminal fluid. In another embodiment, the method further comprises resuspending the precipitated SIgA is in a solution of polyethylene glycol having a molecular weight of 3000 to 30,000 to produce re-precipitated SIgA, and isolating the re-precipitated SIgA. Resuspension and precipitation can be repeated until a pure SIgA composition as described herein is produced.

In one embodiment, the precipitated SIgA composition is pasteurized as described above.

Precipitated pure SIgA can be subjected to additional treatments/purification steps, such as filter sterilization, precipitations using ice cold ethanol (lower than OC to dissolve the PEG and leave only the pure protein), desalting. Other procedures for purification such as sodium sulfate precipitations and gamma carrageenan, and size exclusion chromatography.

In one embodiment, pure or isolated SIgA is prepared from the intestinal mucosa of a pig or a cow. In one embodiment, the preparation of pure or isolated SIgA includes lysing the intestinal mucosa, removing debris by centrifugation, for example, and then proteins in the supernatant are sequentially precipitated using various concentrations of polyethylene glycol (3.5-15% w/v) having a molecular weight of 3000 to 30,000, such that the SIgA will be isolated from other proteins in the mucosa preparation.

In another embodiment, SIgA is in the form of the dried intestinal mucosa of a pig or cow, wherein the intestinal mucosa is not hydrolyzed. In a specific embodiment, the dried intestinal mucosa contains an amount of SIgA effective to increase growth rate and/or improve feed efficiency in an animal. While pig intestinal mucosa has been used previously as a source of amino acids in animal feeds, the intestinal mucosa was hydrolyzed to reduce the constituent proteins to amino acids. The inventors of the present application have unexpectedly discovered that unhydrolyzed, dried pig or cow intestinal mucosa is a source of SIgA. Unhydrolyzed, dried pig or cow intestinal mucosa can be used, for example, as a supplement in animal feed compositions. As used herein, the term unhydrolyzed means that a preparation has not been treated with enzymes, heat (greater than 90° C.) or chemicals under conditions expected to reduce the constituent proteins to amino acids.

In one embodiment, the dried intestinal mucosa is lyophilized, drum dried, or spray dried.

In one embodiment, a method of increasing growth rate, increasing feed efficiency, reducing gastrointestinal inflammation, reducing a risk of gastrointestinal infection, or a combination thereof in a subject, comprises administering to the subject an amount of SIgA effective to increase growth rate, improve feed efficiency, reduce gastrointestinal inflammation, reduce a risk of gastrointestinal infection in the subject, or a combination thereof. Exemplary subjects include humans, avian, porcine, bovine, ovine, capra, fish, reptile, mollusk, invertebrate animal, horse, dog, or cat. The SIgA can be added as pure or isolated SIgA prepared from the intestinal luminal fluid or intestinal mucosa of a pig or cow as described herein. Alternatively, the SIgA is added as unhydrolyzed, dried intestinal mucosa. In one embodiment, the animal is a chicken and the SIgA is administered in the form of an animal food composition comprising the SIgA that has improved feed efficiency compared to a basal food composition. In one embodiment, the animal is a pig and the SIgA is administered in the form of an animal food composition comprising the SIgA that has improved feed efficiency compared to a basal food composition.

In one embodiment, a method of increasing growth rate, improving feed efficiency, reducing gastrointestinal inflammation, reducing a risk of gastrointestinal infection, or a combination thereof in an animal comprises administering to the animal dried intestinal mucosa from a pig or a cow, wherein the dried intestinal mucosa is not hydrolyzed, and wherein the dried intestinal mucosa contains an amount of SIgA effective to increase growth rate, improve feed efficiency, reduce gastrointestinal inflammation, reduce a risk of gastrointestinal infection in the animal, or a combination thereof. Exemplary animals include avian, porcine, bovine, ovine, capra, fish, reptile, mollusk, invertebrate animal, horse, dog, or cat. In one embodiment, the animal is a chicken and the SIgA is administered in the form of an animal food composition comprising the SIgA that has improved feed efficiency compared to a basal food composition.

In another embodiment, a food composition comprises a basal food composition, and an amount of SIgA effective to increase growth rate, improve feed efficiency, reduce gastrointestinal inflammation, reduce a risk of gastrointestinal infection in the animal, or a combination thereof. The amount of SIgA effective to increase growth rate, improve feed efficiency, reduce gastrointestinal inflammation, or reduce a risk of gastrointestinal infection in the animal can be readily determined by one of ordinary skill in the art. For examples, a concentration of greater than 0.1 mg/Kg basal animal or human food is expected to produce beneficial results.

The term "basal food composition" refers to a food composition combinable with additives such as the SIgA compositions described herein. Basal food compositions can be suitable for ingestion by a human or an animal. Exemplary food compositions suitable for ingestion by a human include a nutritionally complete formula, a dairy product, a chilled or shelf stable beverage, a soup, a dietary supplement such as a vitamin, a meal replacement, a nutritional bar, confectionery, or other food composition.

The term "basal animal food composition" refers to an animal food combinable with additives such as the SIgA compositions described herein. Basal animal food compositions may include components such as proteins, grains, flavor compositions, vitamins, minerals, preservatives, and the like. In specific embodiments, the basal animal food composition is for an avian, porcine, bovine, ovine, capra, fish, reptile, mollusk, invertebrate animal, horse, dog, or cat.

In one embodiment, the secretory IgA is in the form of a pure, optionally pasteurized secretory IgA composition isolated from the intestinal luminal fluid of a pig. In a specific embodiment, the pure, pasteurized secretory IgA composition comprises greater than 0.1 mg/Kg basal food composition.

In one embodiment, the basal animal food composition is for a chicken and wherein the animal food composition has improved feed efficiency compared to the basal food composition. In a further embodiment the chicken feed composition comprises 1 mg to 10 g SIgA/Kg chicken feed.

In one embodiment, the SIgA is added to a basal food composition is in the form of dried intestinal mucosa from a pig or a cow, wherein the dried intestinal mucosa is unhydrolyzed. In an embodiment, the concentration is 1 mg/Kg to 10 grams/Kg of the dried intestinal mucosa to the basal animal food composition. In a specific embodiment, the basal food composition is for a chicken and wherein the animal food composition has improved feed efficiency compared to the basal food composition.

Included herein are pharmaceutical compositions comprising pure, pasteurized SIgA and a pharmaceutically acceptable excipient. As used herein, "pharmaceutical composition" means therapeutically effective amounts of the compound together with a pharmaceutically acceptable excipient, such as diluents, preservatives, solubilizers, emulsifiers, and adjuvants. As used herein "pharmaceutically acceptable excipients" are well known to those skilled in the art.

Tablets and capsules for oral administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations which may be used for the drug are conventional formulations well known in the art. Topical administration includes transdermal formulations such as patches.

For topical application to the eye, the inhibitor may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The invention is further illustrated by the following non-limiting examples.

Example 1

Isolation of SIgA from the Luminal Matter of Commercially Slaughtered Pigs

Luminal fluid from commercially slaughtered pigs was collected. Luminal fluid was combined with 3.5% PEG 8000 w/v (Polyethylene glycol 6000-8000 molecular weight) and centrifuged at 14,000×g, 4° C. for 10 minutes. The clarified liquid was collected and filtered through glass wool to remove any fats that may be left. The clarified liquid was then combined with 8.5% PEG 8000 w/v and centrifuged at 14,000×g, 4° C. for 10 minutes. The supernatant was then poured off and the pellet within the tube was resuspended in 12% PEG 8000 w/v in deionized water. The mixture was then centrifuged at 14,000×g, 4° C. for 10 minutes. The supernatant was then poured off and the remaining pellet was frozen at −80° C. and then lyophilized. The purity of the pellet was determined by ELISA. Briefly, 96 well plates were coated with goat anti-pig IgA antibody (120 uL) from Bethyl Laboratories (Montgomery Tex.) dissolved in coating buffer (1.59 g $Na_2CO_3$, 2.93 g $NaHCO_3$, 0.2 g $NaN_3$, pH 9.6, 1000 mL total volume) overnight to allow for attachment of the antibody to the Nunc Maxisorp® F plate (Thermo-Fisher Scientific, Rochester N.Y.). Plates were then blocked with protein free blocking buffer (Pierce, Rockford Ill.) for 1 hour. Plates were then washed 3 times with PBS-0.05% Tween (Fisher-Scientific, Pittsburgh Pa.). Samples were then added to the plate in 10-fold dilutions from 1:10-1:1,000,000,000 to determine the amount of IgA present for 1 hour. Pig reference serum was provided as a control. Plates were then washed 3 times with PBS-0.05% Tween. Goat anti-porcine IgA secondary antibody (Bethyl Laboratories, Montgomery Tex.) was then added in blocking buffer (5 μL 2° antibody: 12.5 mL blocking buffer) for 30 minutes. Plates were washed 6 times with washing buffer. Substrate was then added in substrate buffer (diethanolamine 97 mL, 100 mg $MgCl_2$, 0.2 g $NaN_3$, 800 mL $ddH_2O$, pH 9.8), incubated for 15 minutes then read at 450 nm.

TABLE 1

Amount of IgA isolated from luminal fluid

| Dilution | OD | Protein Amount | |
|---|---|---|---|
| 10 | 1.094 | 1737.572 | |
| 100 | 1.047 | 1100.952 | |
| 1000 | 0.994 | 658.1045 | |
| 10000 | 0.995 | 664.525 | |
| 100000 | 1.04 | 1028.615 | |
| 1000000 | 0.868 | 193.6504 | |
| 10000000 | 0.634 | 19.96927 | 193 and 199 mg/200 mg |
| 100000000 | 0.442 | 3.09598 | |

IgA purity: Luminal fluid (fluid collected from within the intestinal tract through a series of rollers that express intestinal contents without disruption of the mucosal lining) was used and demonstrated greater than 90% purity from the sample. Using 10-fold dilutions there was between 193 and 199 mg of IgA/200 mg of total product.

In a further attempt to quantify the relative purity of IgA, SDS-PAGE was used to determine if there were any contaminates within the IgA. Filter sterilized luminal contents were used, briefly, once the luminal contents finished the final centrifugation, the pellets were hydrated using deionized water and filtered through a 0.2 um stericup filter (Fisher Scientific Pittsburgh Pa.). Once the material was filtered it was lyophilized until needed. The lyophilized powder was then rehydrated using sterilized acidified PBS (pH 4) at a dilution of 1:10 w/v. This stock was then further diluted to 1:1000 and separated on an SDS-PAGE gel and visualized using commassie blue staining. Commassie blue stains all proteins and allows for visualization. 6 unique bands were identified on the gel. Without being held to theory, it is believed that these bands represent the IgA with some contaminants. This gel was sent to the University of Wisconsin-Madison Biotechnology Center for protein sequencing to have yet another way to determine purity of the sample. Four of the six bands found had either IgM or IgA within the top three proteins found. In some cases, within the four bands, IgM and IgA were found in both. This result confirms that a high abundance of antibodies from the lumen of the pig have been isolated. The top two bands were amino-peptidases which are non-specific enzymes. Having the antibody IgM is also very good; IgM is another first responder type antibody. It is the first antibody secreted in response to infection.

TABLE 2

Proteins identified by Protein Sequencing

| | Proteins Identified | Percent Coverage |
|---|---|---|
| Band 1 | glutamyl aminopeptidase | 50 |
| | Porcine Dipeptidyl Peptidase Iv | 56 |
| Band 2 | glutamyl aminopeptidase | 49 |
| | meprin A | 35 |
| | calcium-activated chloride channel regulator 4 | 32 |
| Band 3 | ch4 and secrete domains of swine IgM | 71 |
| | glutamyl aminopeptidase | 46 |
| | aminopeptidase N | 36 |
| Band 4 | ch4 and secrete domains of swine IgM | 73 |
| | Ig alpha chain C region (IgA) | 66 |
| | aminopeptidase N | 47 |
| Band 5 | ch4 and secrete domains of swine IgM | 63 |
| | Ig alpha chain C region (IgA) | 69 |
| | aminopeptidase N | 51 |
| Band 6 | immunoglobulin lambda-chain (Ig light chain) | 65 |
| | Ig alpha chain C region (IgA) | 64 |
| | immunoglobulin heavy chain | 29 |

It was confirmed that IgA was present and in high abundance as fully 50% of the bands had a high quantity of IgA. Interestingly, another important antibody, IgM, was identified in high quantity in fully 50% of the bands found in our filter sterilized luminal fluid. In 83% of bands either IgA or IgM was identified, similar to the assertion of greater than 90% purity using capture ELISA. Sequence coverage is a measure of how much of the protein was sequenced, i.e., 73% of the amino acids in the protein were present. The highest amounts were in IgA and IgM.

Another way to determine IgA in the isolate and also determine if the IgA is active is to use ELISAs to bind IgA to two different substrates, LPS and isolated soy protein. Briefly, 96 well plates were coated with 0.25 g isolated soy protein or 2 mg of E. coli 055:B5 lipopolysaccharide dissolved in coating buffer overnight to allow for attachment of the peptide to the Nunc Maxisorp® F plate (Thermo-Fisher Scientific, Rochester N.Y.). Plates were then blocked with protein free blocking buffer (Pierce, Rockford Ill.) for 1 hour. Plates were then washed 3 times with PBS-0.05% Tween (Fisher-Scientific, Pittsburgh Pa.). Samples were then loaded in 10-fold dilutions from 1:10-1:1,000,000,000 using the freeze dried luminal fluid for 1 hour. Plates were then washed 3 timed with PBS-Tween (0.05%). Goat anti-porcine IgA secondary antibody (Bethyl Laboratories, Montgomery Tex.) was then added in blocking buffer (5 μL 2° antibody: 12.5 mL blocking buffer) for 30 minutes. Plates were washed 6 times with washing buffer. Substrate was then added in substrate buffer (diethanolamine 97 mL, 100 mg $MgCl_2$, 0.2 g $NaN_3$, 800 mL $ddH_2O$, pH 9.8), incubated for 15 minutes then read at 450 nm. Pig serum was used as a control.

TABLE 3

ELISA results of IgA binding to LPS

| | | | |
|---|---|---|---|
| 10 | 0.185 | IgA Control | 0.138 |
| 100 | 1.732 | | |
| 1000 | 0.335 | Background | 0.088 |
| 2000 | 0.182 | | |
| 4000 | 0.138 | | |
| 8000 | 0.124 | | |
| 16000 | 0.102 | | |
| 32000 | 0.08 | | |

Table 3 shows the results for IgA binding to LPS. The control used was 1 μg of IgA isolated from pig serum. The IgA isolated from the lumen needed to be diluted 4000 times to bind the same as control, i.e., there was 4 mg (4000 dilution×1 μg [amount of binding found in the control]) of LPS binding IgA in the lumen of the pig intestines.

TABLE 4

ELISA results of IgA binding to soy protein

| | | | |
|---|---|---|---|
| 10 | 0.244 | IgA Control | 0.075 |
| 100 | 0.823 | | |
| 1000 | 0.313 | Background | 0.0623 |
| 2000 | 0.196 | | |
| 4000 | 0.142 | | |
| 8000 | 0.089 | | |
| 16000 | 0.067 | | |
| 32000 | 0.023 | | |

Table 4 shows the results for IgA binding to isolated soy protein. The control used was 1 ug of IgA isolated from pig serum. The IgA isolated from the lumen needed to be diluted 8000 times to bind the same as control i.e., there was 8 mg of soy protein binding IgA in the lumen of the pig intestines.

Without being held to theory, it is believed that the results from the LPS and soy protein is reasonable since it would be unlikely that there would be more than 5% of the IgA available to bind non-specifically to soy protein and LPS.

Example 2

Pasteurization of IgA Preparation

Pasteurization was used to eliminate bacteria from the IgA preparations. A commercial grade pasteurizer from the University of Wisconsin-Madison Dairy Pilot Plant heated the luminal fluid containing IgA to 121° F. for 20 seconds, and the material was cooled quickly there-after. There was nearly no loss in the amount of IgA and no decrease in the binding capacity of the IgA after pasteurization.

Example 3

SIgA Isolated from Pig Intestinal Lumen Shows Growth Promotion in Commercial Chickens Chick Study #1: All procedures involving animals were approved by the University of Wisconsin Animal Care and Use Committee. One hundred Cornish Rock broiler chicks were purchased from Welp Hatchery (Bancroft Iowa) and divided into groups of at least 50 chicks/group, with chicks divided equally between heat killed IgA (control, IgA heated to 80° C. for 30 minutes) and IgA. Chicks were fed 0.02 g antibody/Kg of feed (either control or IgA). The 0.02 g antibody/Kg feed was fed on top of a complete diet (Sunfresh® Purina, Gray Summit Mo.). Chick weights and feed efficiency were monitored weekly. In this case the IgA was NOT pasteurized.

TABLE 5

Results from chick study one

| | | Week 1 | Week 2 | Week 3 |
|---|---|---|---|---|
| IgA | Weight | 133.32 | 341.16 | 678.3 |
| | Feed Efficiency | 1.43 | 1.75 | 1.75 |
| Control | Weight | 129.68 | 334.16 | 674.9 |
| | Feed Efficiency | 1.43 | 1.76 | 1.76 |
| | | p < 0.2 | | |

Table 5 shows that with unpasteurized IgA fed at 0.02 g/Kg of chicken feed there was no improvement in feed efficiency or weight gain. The improvement in weight gain in the first week but has a p-value of 0.2 and is not considered a successful experiment.

Chick Study #2: One hundred Cornish Rock broiler chicks were purchased from Welp Hatchery (Bancroft Iowa) and divided into groups of at least 50 chicks/group, with chicks divided equally between heat killed IgA (control, IgA heated to 80° C. for 30 minutes) and IgA. Chicks were fed 0.02 g antibody/Kg of feed (either control or IgA). The 0.02 g antibody/Kg feed was fed on top of a complete diet (Sunfresh® Purina, Gray Summit Mo.). Chick weights and feed efficiency were monitored weekly. In this case the IgA was pasteurized.

TABLE 6

Results from chick study two

| | | Week 1 | Week 2 | Week 3 |
|---|---|---|---|---|
| IgA | Weight | 149.34 | 392.7 | 745.61 |
| | Feed Efficiency | 1.51 | 1.71 | 1.75 |
| Control | Weight | 143.72 | 379.56 | 727.76 |
| | Feed Efficiency | 1.62 | 1.79 | 1.79 |
| | | p < 0.05 | p < 0.03 | p < 0.08 |

Without being held to theory, it is believed that pasteurization was the key to this experiment. Comparing the weights from study 1 to study 2, whether you have control or test the weights are higher. IgA promoted growth about 4% and improved feed efficiency about 4.5%. These are relevant numbers for the poultry industry and this experiment should be considered a success.

Example 4

Improvement in Feed Efficiency in Commercial Chickens Using Only the Freeze Dried Mucosa Chick Study with mucosa #1: One hundred Cornish Rock broiler chicks were purchased from Welp Hatchery (Bancroft Iowa) and divided into groups of at least 50 chicks/ group, with chicks divided equally between heat killed mucosa (control, mucosa heated to 80° C. for 30 minutes) and mucosa. Chicks were fed 0.02 g mucosa/Kg of feed (either control or mucosa). The 0.02 g mucosa/Kg feed was fed on top of a complete diet (Sunfresh® Purina, Gray Summit Mo.). Chick weights and feed efficiency were monitored weekly. In this case the mucosa was NOT pasteurized.

TABLE 7

Chick study using freeze dried mucosa

|  |  | Week 1 | Week 2 | Week 3 |
|---|---|---|---|---|
| Mucosa | Weight | 132.18 | 380.44 | 723.95 |
|  | Feed Efficiency | 1.54 | 1.52 | 1.57 |
| Control | Weight | 133.65 | 375.7 | 715.5 |
|  | Feed Efficiency | 1.82 | 1.75 | 1.81 |
|  |  | p < 0.009 | P < 0.01 | p < 0.006 |

The experiment was a success with a 13-16% improvement in feed efficiency. After week one the feed conversion in the controls was not as good as we had seen in four previous trials. However, week 2 and week 3 were close to what was seen in the first two chick trials. Regardless, the feed conversion using the mucosa is 10 points better than the best of the IgA from all the other experiments.

The amount of mucosa in a pig that we measured (3.5 lbs wet weight) was 219.5 grams after lyophilizing. The rate of feeding is equivalent to 20 grams lyophilized mucosa/ton of feed.

Example 5

Isolated of SIgA from Pig Intestinal Mucosa

Mucosa is homogenized in equal parts (50% lysis buffer: 50% mucosa) lysis buffer [50 mmol/L HEPES, 150 mmol/L NaCl, 10% glycerol, 1% Triton X-100, 1.5 mmol/L $MgCl_2$, 10 µg/mL aprotinin, 10 µg/mL leupeptin, 1 mmol/L phenylmethylsulfonyl fluoride (PMSF), 200 µmol/L $Na_3VO_4$, 200 µmol/L NaF, and 1 mmol/L EGTA (final pH 7.5)] overnight at 4° C. 3.5% w/v PEG 8000 is then added to the lysis buffer/mucosa mixture and centrifuged a 14,000×g, 4° C. for 10 minutes. The supernatant is kept then filtered through glass wool. The supernatant is then combined with 8.5% w/v PEG 8000, dissolved, and then centrifuged at 14,000×g, 4° C. for 10 minutes. The supernatant is then discarded and the resulting pellet is resuspended in a dioionized water solution containing 12% PEG 8000 w/v and centrifuged at 14,000×g, 4° C. for 10 minutes. The supernatant is discarded and the resulting pellet is frozen at −80° C. for 1 hour and lyophilized.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A composition comprising
pure, pasteurized secretory IgA isolated from intestinal luminal fluid or intestinal mucosa of a pig or a cow, wherein the pure, pasteurized SIgA composition has an *E. coli* 055:B5 lipopolysaccharide binding activity at least 5 times greater than pig or cow serum IgA *E. coli* 055:B5 lipopolysaccharide binding activity.

2. The composition of claim 1, wherein the pure secretory IgA is greater than 75% pure.

3. The composition of claim 1, in the form of a pharmaceutical composition further comprising a pharmaceutically acceptable excipient.

4. A composition comprising
secretory IgA isolated from a source that is intestinal mucosa of a pig or a cow, wherein the concentration of secretory IgA in the isolated secretory IgA is at least twice the concentration in the source material, wherein the source material is dried intestinal mucosa, an aqueous preparation from intestinal mucosa, or a dry preparation of proteins prepared from intestinal mucosa, wherein the secretory IgA is pasteurized, wherein the pure, pasteurized SIgA composition has an *E. coli* 055:B5 lipopolysaccharide binding activity at least 5 times greater than pig or cow serum IgA *E. coli* 055:B5 lipopolysaccharide binding activity.

5. The composition of claim 4, wherein greater than 5% of the protein in the isolated secretory IgA comprises IgA.

6. The method of claim 1, wherein pasteurization is at 50-100° C. for 30 seconds.

7. The method of claim 1, wherein pasteurization is at 120-150° C. for 1-8 seconds.

8. The method of claim 4, wherein pasteurization is at 50-100° C. for 30 seconds.

9. The method of claim 4, wherein pasteurization is at 120-150° C. for 1-8 seconds.

* * * * *